(12) United States Patent
Larsen

(10) Patent No.: US 12,239,827 B2
(45) Date of Patent: Mar. 4, 2025

(54) DRUG DELIVERY ASSEMBLY WITH INFORMATION CAPTURE

(71) Applicant: Novo Nordisk A/S, Bagsvaerd (DK)

(72) Inventor: Andre Larsen, Dragoer (DK)

(73) Assignee: Novo Nordisk A/S, Bagsvaerd (DK)

( * ) Notice: Subject to any disclaimer, the term of this patent is extended or adjusted under 35 U.S.C. 154(b) by 1142 days.

(21) Appl. No.: 17/056,319

(22) PCT Filed: May 16, 2019

(86) PCT No.: PCT/EP2019/062645
§ 371 (c)(1),
(2) Date: Nov. 17, 2020

(87) PCT Pub. No.: WO2019/219825
PCT Pub. Date: Nov. 21, 2019

(65) Prior Publication Data
US 2021/0228809 A1   Jul. 29, 2021

(30) Foreign Application Priority Data

May 18, 2018  (EP) .................................... 18173083

(51) Int. Cl.
*A61M 5/315* (2006.01)
*A61M 5/31* (2006.01)

(52) U.S. Cl.
CPC .... *A61M 5/31553* (2013.01); *A61M 5/31568* (2013.01); *A61M 2005/3126* (2013.01);
(Continued)

(58) Field of Classification Search
CPC .......... A61M 5/31553; A61M 5/31568; A61M 5/3157; A61M 2005/3126;
(Continued)

(56) References Cited

U.S. PATENT DOCUMENTS

| 7,008,399 B2 | 3/2006 | Larsen et al. |
| 9,354,725 B2 | 5/2016 | Al-Sharif et al. |

(Continued)

FOREIGN PATENT DOCUMENTS

| WO | 2010052275 A2 | 5/2010 |
| WO | WO-2010052275 * | 5/2010 |

(Continued)

OTHER PUBLICATIONS

Moreno et al., "Experimental Characterization of the Twin-Eye Laser Mouse Sensor," Hindawi Publishing Corporation, Journal of Sensors, vol. 2016, Article ID 4281397, pp. 1-8, http:/dx.doi.org/10.1155/2016/4281397.

*Primary Examiner* — Theodore J Stigell
(74) *Attorney, Agent, or Firm* — Wesley Nicolas

(57) ABSTRACT

A drug delivery assembly comprising an indicator adapted to move during expelling of a dose amount of drug, the amount of movement being indicative of the size of the expelled dose amount, and electronic tracking sensor circuitry adapted to with pre-determined intervals to change the operative state from a sleep state to a low-power detection state and back to the sleep state. When in the detection state, the electronic sensor circuitry is adapted to detect motion of an activation component, and if motion of the activation component is detected, then change the operative state from the low-power detection state to a high-power measuring state in which the amount of motion of the indicator relative to the tracking means can be determined.

15 Claims, 9 Drawing Sheets

(52) U.S. Cl.
CPC ....... *A61M 5/3157* (2013.01); *A61M 2205/18* (2013.01); *A61M 2205/3306* (2013.01)

(58) Field of Classification Search
CPC ...... A61M 2205/18; A61M 2205/3306; A61M 2205/3561; A61M 2205/502; A61M 5/24
See application file for complete search history.

(56) References Cited

U.S. PATENT DOCUMENTS

| | | |
|---|---|---|
| 2009/0318865 A1 | 12/2009 | Moller et al. |
| 2012/0022458 A1 | 1/2012 | Oh et al. |
| 2016/0030673 A1 | 2/2016 | White et al. |
| 2017/0331252 A1 | 11/2017 | Schemmann |

FOREIGN PATENT DOCUMENTS

| | | | |
|---|---|---|---|
| WO | 2014111340 A1 | | 7/2014 |
| WO | 2014128157 A1 | | 8/2014 |
| WO | WO-2014128157 | * | 8/2014 |
| WO | 2017009724 A1 | | 1/2017 |
| WO | 2017148857 A1 | | 9/2017 |
| WO | 2018013843 A1 | | 1/2018 |

* cited by examiner

DRUG DELIVERY ASSEMBLY WITH INFORMATION CAPTURE

CROSS-REFERENCE TO RELATED APPLICATIONS

This application is a 35 U.S.C. § 371 National Stage application of International Application PCT/EP2019/062645 (published as WO 2019/219825), filed May 16, 2019, which claims priority to European Patent Application 18173083.9, filed May 18, 2018, the contents of all above-named applications are incorporated herein by reference.

The present invention relates to drug delivery assemblies, devices and systems adapted for capturing drug delivery related data in a cost-effective way.

BACKGROUND OF THE INVENTION

In the disclosure of the present invention reference is mostly made to the treatment of diabetes by delivery of insulin, however, this is only an exemplary use of the present invention.

Drug injection devices have greatly improved the lives of patients who must self-administer drugs and biological agents. Drug injection devices may take many forms, including simple disposable devices that are little more than an ampoule with an injection means or they may be durable devices adapted to be used with pre-filled cartridges. Regardless of their form and type, they have proven to be great aids in assisting patients to self-administer injectable drugs and biological agents. They also greatly assist care givers in administering injectable medicines to those incapable of performing self-injections.

Performing the necessary insulin injection at the right time and in the right size is essential for managing diabetes, i.e. compliance with the specified insulin regimen is important. In order to make it possible for medical personnel to determine the effectiveness of a prescribed dosage pattern, diabetes patients are encouraged to keep a log of the size and time of each injection. However, such logs are normally kept in handwritten notebooks, from where the logged information may not be easily uploaded to a computer for data processing. Furthermore, as only events, which are noted by the patient, are logged, the note book system requires that the patient remembers to log each injection, if the logged information is to have any value in the treatment of the patient's disease. A missing or erroneous record in the log results in a misleading picture of the injection history and thus a misleading basis for the medical personnel's decision making with respect to future medication. Accordingly, it may be desirable to automate the logging of ejection information from medication delivery systems.

Correspondingly, a number of injection devices with a dose monitoring/acquisition feature have been provided, see e.g. US 2009/0318865, WO 2010/052275 and U.S. Pat. No. 7,008,399. However, most devices of today are without it.

In respect of devices with a non-replaceable energy source, e.g. a disposable drug delivery device, such a device may only be used for a relatively short period e.g. a few weeks, but typically have a much longer shelve-life. An expected shelve-life of up to three years is not unusual. Thus, power management is very important to keep price and accommodation space requirements low. WO 2010/052275 discloses a drug delivery device with dose logging circuitry comprising a Gray code type rotary sensor. The device comprises a number of contacts allowing an operational state to be detected wherein the device enters a high-power state in which the rotary sensor is operated to determine the size of an expelled dose. WO 2014/111340 discloses a drug delivery device comprising optical sensors adapted to detect whether the device is in a dose setting or dose expelling state and to determine the size of an expelled dose. A switch is provided to turn on the optical sensors.

Having regard to the above, it is an object of the present invention to provide a drug delivery device and system as well as components therefore which cost-effectively and reliably allows detection, storage and/or display of data related to use of a drug delivery device.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first aspect of the invention a drug delivery assembly is provided comprising a housing, a drug reservoir or means for receiving a drug reservoir, an activation indicator and drug expelling means. The drug expelling means comprises dose setting means allowing a user to set a dose amount of drug to be expelled, and release means which when actuated causes movement of the activation indicator and the drug expelling means to expel a set dose. The drug delivery assembly further comprises a dose indicator adapted to move during expelling of a dose amount of drug, the amount of movement being indicative of the size of the expelled dose amount, and electronic sensor circuitry adapted to detect the amount of movement of the dose indicator during expelling of a dose amount. The electronic sensor circuitry comprises a light-based non-contact tracking means adapted to determine a motion property of a surface moved relative to the tracking means. The electronic sensor circuitry is adapted to be operated between a sleep state, a low power detection state allowing a first motion property to be determined, and a high power measuring state allowing a second motion property to be determined. The electronic sensor circuitry is adapted to change the operative state from the sleep state to the detection state and back to the sleep state with pre-determined intervals. Such a mode could be characterized as an idle mode. When in the detection state, the electronic sensor circuitry is adapted to detect whether motion of the activation indicator relative to the tracking means takes place, and if motion of the activation indicator is detected, the electronic sensor circuitry is adapted to change the operative state from the detection state to the measuring state in which the amount of motion of the dose indicator relative to the tracking means can be determined.

By this arrangement an expelled dose amount can be determined in a simple and power efficient way as motion determination is based on movement of surfaces and do not rely on specific detection structures as switches or encoders, the latter adding to both cost and complexity of a given drug delivery device. Further, by implementing a sensor set-up which can be operated at different power levels dependent upon the actual requirement for the property to be detected, a set-up can be provided which is not just simple but also power efficient.

The drug expelling means (mechanism) may comprise a spring which is strained during dose setting and then released to drive a piston rod when the release means (button) is actuated. Alternatively, the expelling mechanism may be a fully manual device of the type in which a dose setting member and an actuation button move proximally during dose setting corresponding to the set dose size. When the user subsequently pushes the actuation button axially in the distal direction a dose coupling is actuated allowing the dose setting member to be rotationally moved distally to expel the set dose. As appears, in both designs the activation indicator is moved just prior to the dose indicator is actuated to rotate.

The light-based non-contact tracking means may e.g. be laser-based with the dose indicator and activation indicator comprising light-scattering surfaces towards which the laser light can be directed.

The terms "low power state" and "high power state" indicate power consumption states allowing the defined kind of motion for the given indicator to be detected. The actual power consumption will be determined by factors such as sensor intensity level, sampling rate and the nature of the surface and material of the indicator. For example, in an exemplary embodiment the electronic sensor circuitry when in the low power detection state is operated to detect motion with a low resolution, and when in the high power measuring is operated to detect motion with a high resolution.

The defined first motion property could simply be in the form of "recognizing movement" with the sensor circuitry being adapted to determine whether a given structure is moving or not. The defined second motion property could be in the form of "amount of movement", e.g. the actual distance a given structure has been moved in a given direction.

The term "indicator" refers to a surface of a component adapted to move in response to an activity as specified above. The dose indicator and the activation indicator surfaces may be arranged on the same or different components. In the former case the two indicator surfaces may be fully or partly overlapping. For example, a "combined indicator" could be formed by a component having a surface wherein movement in a first direction would function as a first indicator and movement in a second direction would function as a second indicator.

Depending on the actual design of the electronic circuitry and the capacity of the power source, it may be possible to allow the sensor circuitry to wake up from the sleep state to detect for movement also during shelf storage, e.g. during 2 or 3 years. Alternatively, a traditional pullout strip may be used to allow the electronics to power-up before initial use.

In an exemplary embodiment the indicator rotates during dose expelling, the electronic sensor circuitry being adapted to determine the amount of rotation.

The dose setting means may comprise a dose setting member adapted to be rotated by a user to set a dose, with the drug expelling means further comprising a release member actuatable between a proximal position and a distal position, the proximal position allowing a dose amount to be set by rotation of the dose setting member, the distal position allowing the drug expelling means to expel a set dose.

In such an embodiment rotation of the dose setting member may cause motion of the activation indicator, e.g. the dose setting member per se may be used as an activation indicator. Alternatively, actuation of the release member may, directly or indirectly, cause motion of the activation indicator.

In an exemplary embodiment the dose indicator rotates during dose expelling relative to a reference axis and the activation indicator moves axially relative to the reference axis. The activation indicator and the dose indicator may be coupled to each other forming a combined indicator, i.e. moving axially and rotationally together. The combined indicator may be in the form of a common component in which fully or partly overlapping surface portions serve as the two indicators.

In a further exemplary embodiment, the drug expelling means comprises an alert indicator adapted to move during dose setting, the electronic sensor circuitry being adapted to be operated between an idle mode and an alert mode. When in the idle mode, the electronic sensor circuitry is adapted to change, with pre-determined intervals, the operative state from the sleep state to the detection state and back to the sleep state. When in the idle mode and in the detection state, the electronic sensor circuitry is adapted to detect motion of the alert indicator relative to the tracking means, and if motion of the alert indicator relative to the tracking means is detected, then change the idle mode to the alert mode in which the electronic sensor circuitry with shortened intervals changes the operative state from the sleep state to the detection state and back to the sleep state. When in the alert mode and in the detection state, the electronic sensor circuitry is adapted to detect motion of the activation indicator relative to the tracking means, and if motion of the activation indicator relative to the tracking means is detected, then change the operative state from the detection state to the measuring state in which the amount of motion of the dose indicator relative to the tracking means can be determined.

The actual power consumption when the sensor circuitry is "on" in the idle respectively the alert mode may be the same or different. Although the object of both modes is to detect "motion" of an indicator, the actual expected speed of motion as well as the properties of the indicator surfaces may result in the sensor being operated differently when active, e.g. with a higher or lower intensity of a laser sensor.

By this arrangement an additional "mid-level" of power consumption (corresponding to the alert mode) has been introduced, this allowing the power consumption levels to be optimized to the given movement patterns for the indicators embodied in a given specific design for a drug delivery assembly. For example, the activation indicator may relatively fast travel a relatively short distance before the dose indicator starts to move, which in a two-level power set-up would prevent the sensor to power up at a "very low" rate. However, in many drug delivery device designs an "alert indicator" can be identified which in a typical use scenario may travel relatively slowly a relatively long distance before the activation indicator starts to move, this allowing the sensor circuitry in the idle mode to operate at a desirable "very low" rate. After a given amount of time and without detection of movement of the activation indicator the alert mode will change back to the idle mode. Thus, in a specific embodiment the alert indicator rotates during dose setting.

Corresponding to the above-described combined indicator, at least two of the alert indicator, the activation indicator and the dose indicator may be coupled to each other forming a combined indicator.

For example, when rotation of a dose setting member causes motion of the activation component, and when actuation of a release member causes motion of the activation component (as disclosed above), the indicator may also serve as the alert component and the activation component, the indicator having a first orientation of movement during setting and expelling of a dose amount, and a second orientation of movement when actuated by the release member. The first orientation of movement may be rotation relative to the housing and reference axis, and the second orientation of movement may be axial movement relative to the housing and reference axis.

In an exemplary embodiment the drug delivery assembly is of a unitary design with the drug expelling means and the electronic sensor circuitry being both arranged within the housing. Alternatively, the electronic sensor circuitry may be in the form of an "electronic label" comprising a flexible sheet attached to an outer surface of a drug delivery device. The label may be provided with a display, e.g. of the printed ink-type which mainly uses energy when changing state. An antenna may also be formed on the flexible sheet by printing, the processor being adapted to transmit data to an external receiver via the antenna.

In an alternative configuration, the assembly may comprise a drug delivery device and an add-on device adapted to be releasably mounted thereon, the drug delivery device comprising the drug expelling means and the indicators, the add-on device comprising the electronic sensor circuitry.

In the latter case a given type of drug delivery device, e.g. a FlexTouch® pre-filled drug delivery pen as manufactured and sold by Novo Nordisk A/S, Bagsværd, Denmark, may be used for a number of different drugs, each version being adapted to be use together with the above-described add-on dose logging device. However, for a given drug and a given drug formulation a given amount of movement of the indicator may be indicative of different amounts of drug. For example, a given rotational movement of one of the expelling components in a FlexTouch® device, e.g. the reset tube (see below), for a U200 insulin formulation would be indicative of an expelled dose amount twice as high as for a U100 insulin formulation.

Correspondingly, an add-on dose logging device as described above may be provided with detection means allowing an identifier comprised in the drug delivery device to be identified, the identifier coding for the actual type of drug contained in the (prefilled) drug delivery device. The code may e.g. be in the form of a visual code such as a colour or a bar or matrix code.

The electronic sensor circuitry may be provided with visual communication means in the form of a display adapted to display dose related data, the display being controlled by the electronic processor circuitry. The drug delivery device may further comprise a memory adapted to store dose related data, the memory being controlled by the electronic processor circuitry. In addition or alternatively, the electronic sensor circuitry may be provided with data communication means adapted to transmit or transfer dose related data to an auxiliary or external device, e.g. a smartphone running a corresponding app.

In the above disclosure of the invention a drug delivery assembly is described comprising drug expelling means having dose setting means allowing a user to set a dose amount of drug to be expelled. In an alternative configuration the drug expelling means is adapted to expel a fixed-size dose. Indeed, in such a configuration the electronic sensor circuitry would essentially detect the same dose size for each out-dosing event, however, this could be used as a confirmation that the intended dose size was expelled correctly.

As used herein, the term "drug" is meant to encompass any flowable medicine formulation capable of being passed through a delivery means such as a cannula or hollow needle in a controlled manner, such as a liquid, solution, gel or fine suspension, and containing one or more drug agents. The drug may be a single drug compound or a premixed or co-formulated multiple drug compounds drug agent from a single reservoir. Representative drugs include pharmaceuticals such as peptides (e.g. insulins, insulin containing drugs, GLP-1 containing drugs as well as derivatives thereof), proteins, and hormones, biologically derived or active agents, hormonal and gene based agents, nutritional formulas and other substances in both solid (dispensed) or liquid form. In the description of the exemplary embodiments reference will be made to the use of insulin and GLP-1 containing drugs, this including analogues thereof as well as combinations with one or more other drugs.

BRIEF DESCRIPTION OF THE DRAWINGS

In the following embodiments of the invention will be described with reference to the drawings, wherein.

In the figures like structures are mainly identified by like reference numerals.

DESCRIPTION OF EXEMPLARY EMBODIMENTS

Figure 1A:
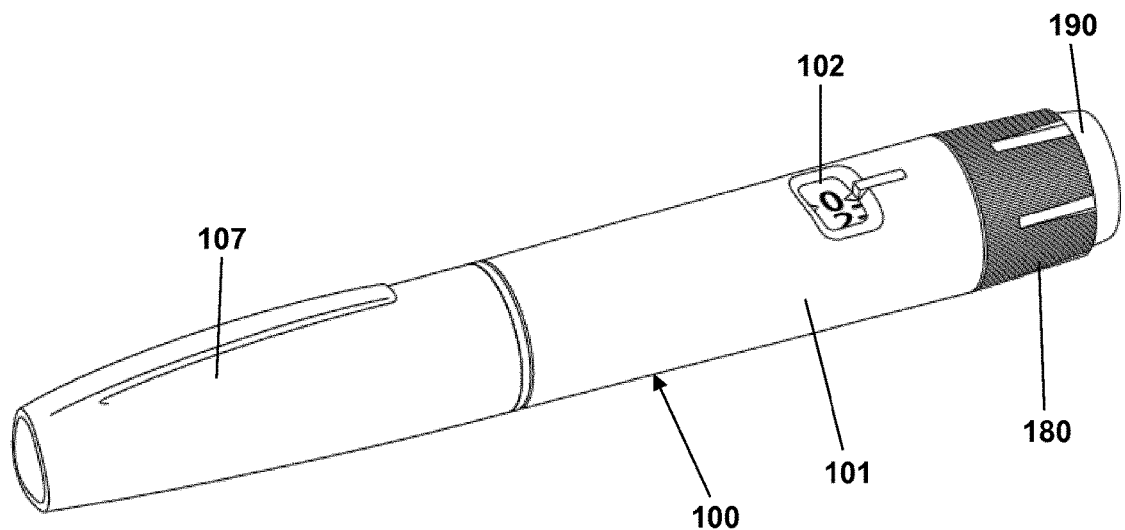
FIG. 1A shows a pen device.

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. The terms "assembly" and "subassembly" do not imply that the described components necessarily can be assembled to provide a unitary or functional assembly or subassembly during a given assembly procedure but is merely used to describe components grouped together as being functionally more closely related.

Before turning to embodiments of the present invention per se, an example of a pre-filled drug delivery will be described, such a device providing the basis for the exemplary embodiments of the present invention. Although the pen-formed drug delivery device 100 shown in FIG. 1 represents a "generic" drug delivery device, the actually shown device is a FlexTouch® prefilled drug delivery pen as manufactured and sold by Novo Nordisk A/S, Bagsværd, Denmark.

The pen device 100 comprises a cap part 107 and a main part having a proximal body or drive assembly portion with a housing 101 in which a drug expelling mechanism is arranged or integrated, and a distal cartridge holder portion in which a drug-filled transparent cartridge 113 with a distal needle-penetrable septum is arranged and retained in place by a non-removable cartridge holder attached to the proximal portion, the cartridge holder having openings allowing a portion of the cartridge to be inspected as well as distal coupling means 115 allowing a needle assembly to be releasably mounted. The cartridge is provided with a piston driven by a piston rod forming part of the expelling mechanism and may for example contain an insulin, GLP-1 or growth hormone formulation. A proximal-most rotatable dose setting member 180 serves to manually set a desired dose of drug shown in display window 102 and which can then be expelled when the button 190 is actuated. Depending on the type of expelling mechanism embodied in the drug delivery device, the expelling mechanism may comprise a spring as in the shown embodiment which is strained during dose setting and then released to drive the piston rod when the release button is actuated. Alternatively the expelling mechanism may be fully manual in which case the dose member and the actuation button moves proximally during dose setting corresponding to the set dose size, and then is moved distally by the user to expel the set dose, e.g. as in a FlexPen® manufactured and sold by Novo Nordisk A/S.

Figure 1B:
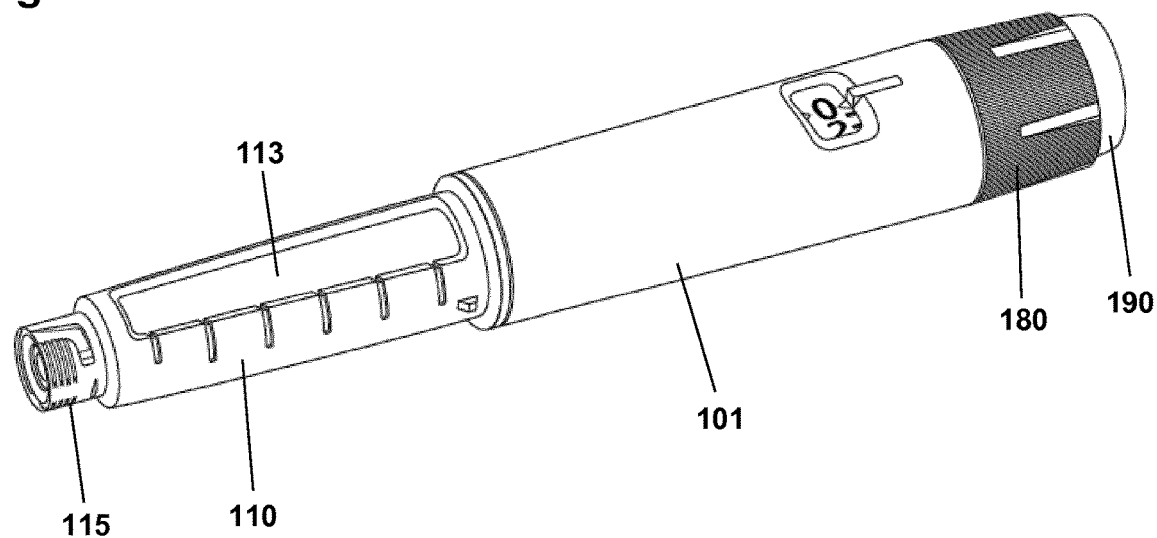
FIG. 1B shows the pen device of FIG. 1A with the pen cap removed.

Although FIG. 1 shows a drug delivery device of the pre-filled type, i.e. it is supplied with a premounted cartridge and is to be discarded when the cartridge has been emptied, in alternative embodiments the drug delivery device may be designed to allow a loaded cartridge to be replaced, e.g. in the form of a "rear-loaded" drug delivery device in which the cartridge holder is adapted to be removed from the device main portion, or alternatively in the form of a "frontloaded" device in which a cartridge is inserted through a distal opening in the cartridge holder which is non-removable attached to the main part of the device.

As the invention relates to electronic circuitry adapted to interact with a drug delivery device by incorporation or by being mounted thereon, an exemplary embodiment of such a device will be described for better understanding of the invention.

Figure 2:
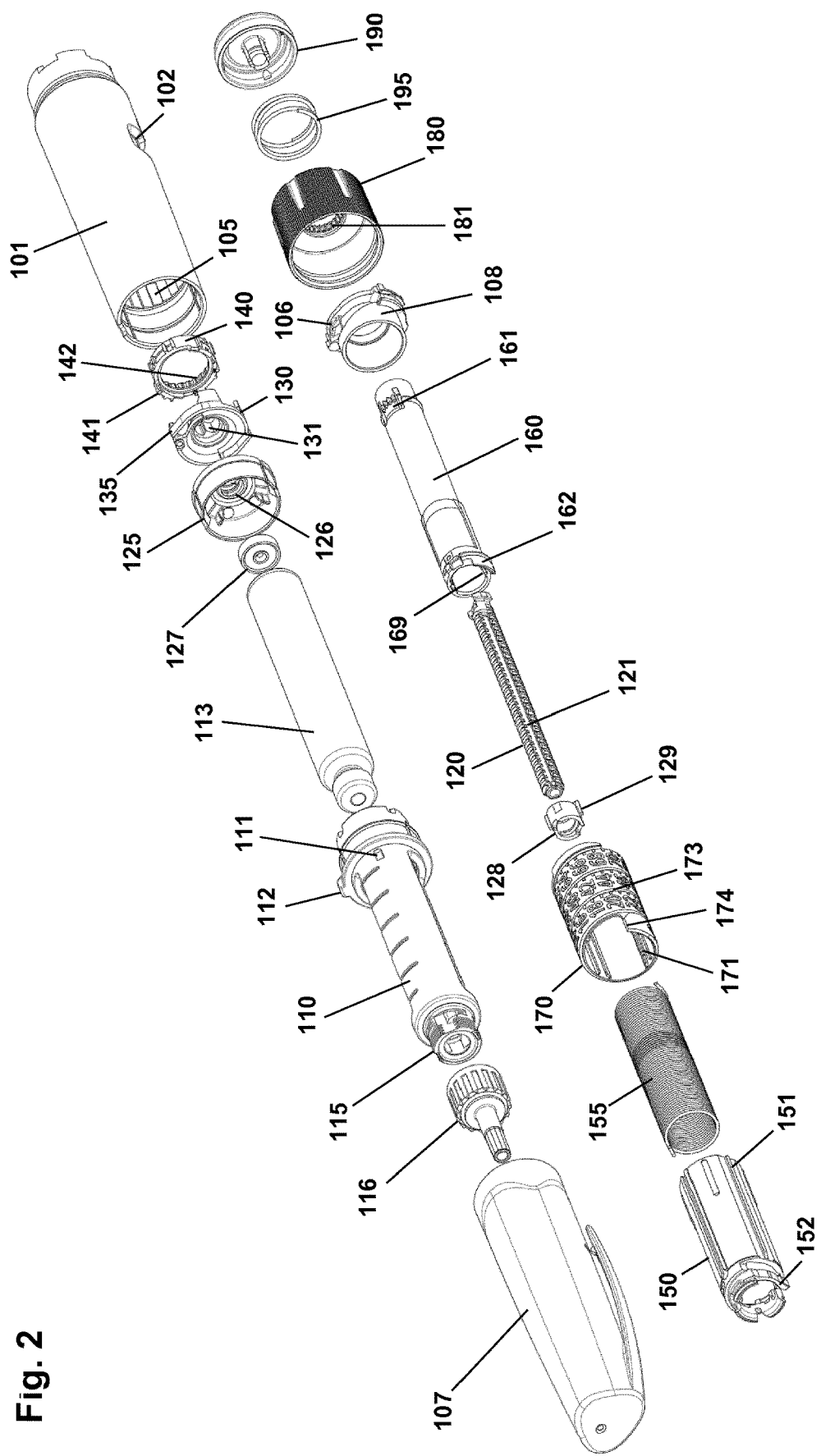
FIG. 2 shows in an exploded view the components of the pen device of FIG. 1A, FIGS. 3A and 3B show in sectional views an expelling mechanism in two states.

FIG. 2 shows an exploded view of the pen-formed drug delivery device 100 shown in FIG. 1. More specifically, the pen comprises a tubular housing 101 with a window opening 102 and onto which a cartridge holder 110 is fixedly mounted, a drug-filled cartridge 113 being arranged in the cartridge holder. The cartridge holder is provided with distal coupling means 115 allowing a needle assembly 116 to be releasably mounted, proximal coupling means in the form of two opposed protrusions 111 allowing a cap 107 to be releasably mounted covering the cartridge holder and a mounted needle assembly, as well as a protrusion 112 preventing the pen from rolling on e.g. a table top. In the housing distal end a nut element 125 is fixedly mounted, the nut element comprising a central threaded bore 126, and in the housing proximal end a spring base member 108 with a central opening is fixedly mounted. A drive system comprises a threaded piston rod 120 having two opposed longitudinal grooves and being received in the nut element threaded bore, a ring-formed piston rod drive element 130 rotationally arranged in the housing, and a ring-formed clutch element 140 which is in rotational engagement with the drive element (see below), the engagement allowing axial movement of the clutch element. The clutch element is provided with outer spline elements 141 adapted to engage corresponding splines 104 (see FIG. 4B) on the housing inner surface, this allowing the clutch element to be moved between a rotationally locked proximal position, in which the splines are in engagement, and a rotationally free distal position in which the splines are out of engagement. As just mentioned, in both positions the clutch element is rotationally locked to the drive element. The drive element comprises a central bore with two opposed protrusions 131 in engagement with the grooves on the piston rod whereby rotation of the drive element results in rotation and thereby distal axial movement of the piston rod due to the threaded engagement between the piston rod and the nut element. The drive element further comprises a pair of opposed circumferentially extending flexible ratchet arms 135 adapted to engage corresponding ratchet teeth 105 arranged on the housing inner surface. The drive element and the clutch element comprise cooperating coupling structures rotationally locking them together but allowing the clutch element to be moved axially, this allowing the clutch element to be moved axially to its distal position in which it is allowed to rotate, thereby transmitting rotational movement from the dial system (see below) to the drive system. The interaction between the clutch element, the drive element and the housing will be shown and described in greater detail with reference to FIGS. 4A and 4B.

On the piston rod an end-of-content (EOC) member 128 is threadedly mounted and on the distal end a washer 127 is rotationally mounted. The EOC member comprises a pair of opposed radial projections 129 for engagement with the reset tube (see below).

The dial system comprises a ratchet tube 150, a reset tube 160, a scale drum 170 with an outer helically arranged row of dose numerals, a user-operated dial member 180 for setting a dose of drug to be expelled, a release button 190 and a torque spring 155 (see FIG. 3). The reset tube is mounted axially locked inside the ratchet tube but is allowed to rotate a few degrees (see below). The reset tube comprises on its inner surface two opposed longitudinal grooves 169 adapted to engage the radial projections 129 of the EOC member, whereby the EOC can be rotated by the reset tube but is allowed to move axially. The clutch element is mounted axially locked on the outer distal end portion of the ratchet tube 150, this providing that the ratchet tube can be moved axially in and out of rotational engagement with the housing via the clutch element. The dial member 180 is mounted axially locked but rotationally free on the housing proximal end, the dial ring being under normal operation rotationally locked to the reset tube (see below), whereby rotation of dial ring results in a corresponding rotation of the reset tube and thereby the ratchet tube. The release button 190 is axially locked to the reset tube but is free to rotate. A return spring 195 provides a proximally directed force on the button and the thereto mounted reset tube. The scale drum 170 is arranged in the circumferential space between the ratchet tube and the housing, the drum being rotationally locked to the ratchet tube via cooperating longitudinal splines 151, 171 and being in rotational threaded engagement with the inner surface of the housing via cooperating thread structures 103, 173, whereby the row of numerals passes the window opening 102 in the housing when the drum is rotated relative to the housing by the ratchet tube. The torque spring is arranged in the circumferential space between the ratchet tube and the reset tube and is at its proximal end secured to the spring base member 108 and at its distal end to the ratchet tube, whereby the spring is strained when the ratchet tube is rotated relative to the housing by rotation of the dial member. A ratchet mechanism with a flexible ratchet arm 152 is provided between the ratchet tube and the clutch element, the latter being provided with an inner circumferential teeth structures 142, each tooth providing a ratchet stop such that the ratchet tube is held in the position to which it is rotated by a user via the reset tube when a dose is set. In order to allow a set dose to be reduced a ratchet release mechanism 162 is provided on the reset tube and acting on the ratchet tube, this allowing a set dose to be reduced by one or more ratchet increments by turning the dial member in the opposite direction, the release mechanism being actuated when the reset tube is rotated the above-described few degrees relative to the ratchet tube.

Figure 3A:
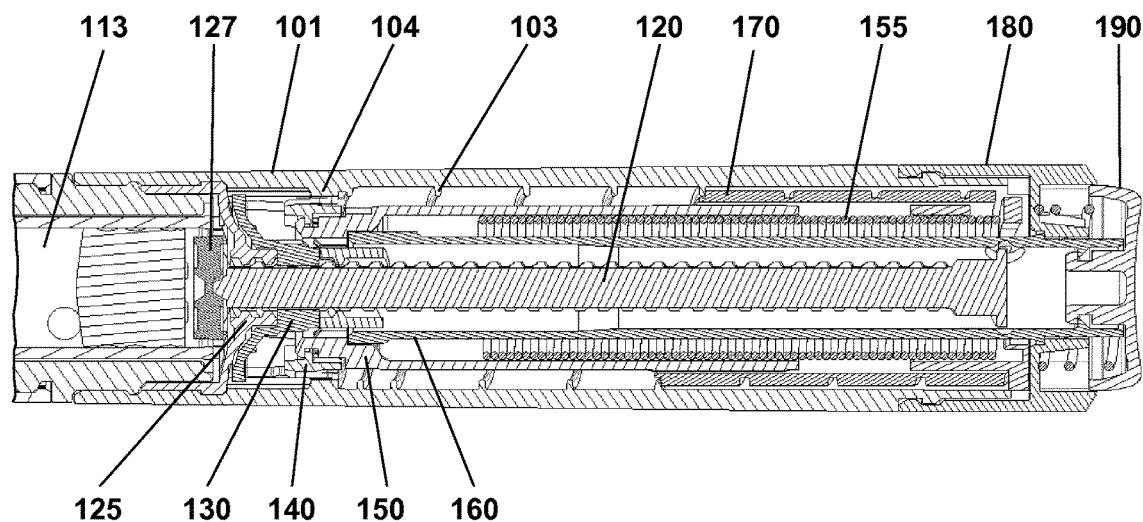

Having described the different components of the expelling mechanism and their functional relationship, operation of the mechanism will be described next with reference mainly to FIGS. 3A and 3B.

The pen mechanism can be considered as two interacting systems, a dose system and a dial system, this as described above. During dose setting the dial mechanism rotates and the torsion spring is loaded. The dose mechanism is locked to the housing and cannot move. When the push button is pushed down, the dose mechanism is released from the housing and due to the engagement to the dial system, the torsion spring will now rotate back the dial system to the starting point and rotate the dose system along with it.

The central part of the dose mechanism is the piston rod 120, the actual displacement of the plunger being performed by the piston rod. During dose delivery, the piston rod is rotated by the drive element 130 and due to the threaded interaction with the nut element 125 which is fixed to the housing, the piston rod moves forward in the distal direction. Between the rubber piston and the piston rod, the piston washer 127 is placed which serves as an axial bearing for the rotating piston rod and evens out the pressure on the rubber piston. As the piston rod has a non-circular cross section where the piston rod drive element engages with the piston rod, the drive element is locked rotationally to the piston rod, but free to move along the piston rod axis. Consequently, rotation of the drive element results in a linear forwards movement of the piston. The drive element is provided with small ratchet arms 134 which prevent the drive element from rotating clockwise (seen from the push button end). Due to the engagement with the drive element, the piston rod can thus only move forwards. During dose delivery, the drive element rotates anti-clockwise and the ratchet arms 135 provide the user with small clicks due to the engagement with the ratchet teeth 105, e.g. one click per unit of insulin expelled.

Turning to the dial system, the dose is set and reset by turning the dial member 180. When turning the dial, the reset tube 160, the EOC member 128, the ratchet tube 150 and the scale drum 170 all turn with it. As the ratchet tube is connected to the distal end of the torque spring 155, the spring is loaded. During dose setting, the arm 152 of the ratchet performs a dial click for each unit dialled due to the interaction with the inner teeth structure 142 of the clutch element. In the shown embodiment the clutch element is provided with 24 ratchet stops providing 24 clicks (increments) for a full 360 degrees rotation relative to the housing. The spring is preloaded during assembly which enables the mechanism to deliver both small and large doses within an acceptable speed interval. As the scale drum is rotationally engaged with the ratchet tube, but movable in the axial direction and the scale drum is in threaded engagement with the housing, the scale drum will move in a helical pattern when the dial system is turned, the number corresponding to the set dose being shown in the housing window 102.

The ratchet 152, 142 between the ratchet tube and the clutch element 140 prevents the spring from turning back the parts. During resetting, the reset tube moves the ratchet arm 152, thereby releasing the ratchet click by click, one click corresponding to one unit IU of insulin in the described embodiment. More specifically, when the dial member is turned clockwise, the reset tube simply rotates the ratchet tube allowing the arm of the ratchet to freely interact with the teeth structures 142 in the clutch element. When the dial member is turned counter-clockwise, the reset tube interacts directly with the ratchet click arm forcing the click arm towards the centre of the pen away from the teeth in the clutch, thus allowing the click arm on the ratchet to move "one click" backwards due to torque caused by the loaded spring.

Figure 3B:
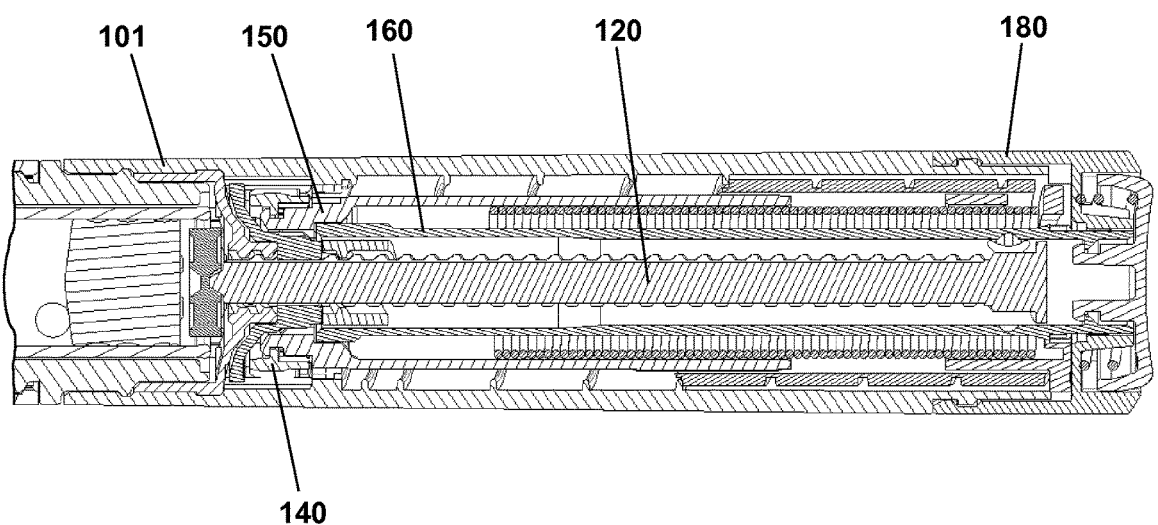

To deliver a set dose, the push button 190 is pushed in the distal direction by the user as shown in FIG. 3B. The reset tube 160 decouples from the dial member and subsequently the clutch element 140 disengages the housing splines 104. Now the dial mechanism returns to "zero" together with the drive element 130, this leading to a dose of drug being expelled. It is possible to stop and start a dose at any time by releasing or pushing the push button at any time during drug delivery. A dose of less than 5 IU normally cannot be paused, since the rubber piston is compressed very quickly leading to a compression of the rubber piston and subsequently delivery of insulin when the piston returns to the original dimensions.

The EOC feature prevents the user from setting a larger dose than left in the cartridge. The EOC member 128 is rotationally locked to the reset tube, which makes the EOC member rotate during dose setting, resetting and dose delivery, during which it can be moved axially back and forth following the thread of the piston rod. When it reaches the proximal end of the piston rod a stop is provided, this preventing all the connected parts, including the dial member, from being rotated further in the dose setting direction, i.e. the now set dose corresponds to the remaining drug content in the cartridge.

The scale drum 170 is provided with a distal stop surface 174 adapted to engage a corresponding stop surface on the housing inner surface, this providing a maximum dose stop for the scale drum preventing all the connected parts, including the dial member, from being rotated further in the dose setting direction. In the shown embodiment the maximum dose is set to 80 IU. Correspondingly, the scale drum is provided with a proximal stop surface adapted to engage a corresponding stop surface on the spring base member, this preventing all the connected parts, including the dial member, from being rotated further in the dose expelling direction, thereby providing a "zero" stop for the entire expelling mechanism.

To prevent accidental over-dosage in case something should fail in the dialling mechanism allowing the scale drum to move beyond its zero-position, the EOC member serves to provide a security system. More specifically, in an initial state with a full cartridge the EOC member is positioned in a distal-most axial position in contact with the drive element. After a given dose has been expelled the EOC member will again be positioned in contact with the drive element. Correspondingly, the EOC member will lock against the drive element in case the mechanism tries to deliver a dose beyond the zero-position. Due to tolerances and flexibility of the different parts of the mechanism the EOC will travel a short distance allowing a small "over dose" of drug to be expelled, e.g. 3-5 IU of insulin.

The expelling mechanism further comprises an end-of-dose (EOD) click feature providing a distinct feedback at the end of an expelled dose informing the user that the full amount of drug has been expelled. More specifically, the EOD function is made by the interaction between the spring base and the scale drum. When the scale drum returns to zero, a small click arm 106 on the spring base is forced backwards by the progressing scale drum. Just before "zero" the arm is released and the arm hits a countersunk surface on the scale drum.

The shown mechanism is further provided with a torque limiter in order to protect the mechanism from overload applied by the user via the dial member. This feature is provided by the interface between the dial member and the reset tube which as described above are rotationally locked to each other. More specifically, the dial member is provided with a circumferential inner teeth structure 181 engaging a number of corresponding teeth arranged on a flexible carrier portion 161 of the reset tube. The reset tube teeth are designed to transmit a torque of a given specified maximum size, e.g. 150-300 Nmm, above which the flexible carrier portion and the teeth will bend inwards and make the dial member turn without rotating the rest of the dial mechanism. Thus, the mechanism inside the pen cannot be stressed at a higher load than the torque limiter transmits through the teeth.

Figure 4A:
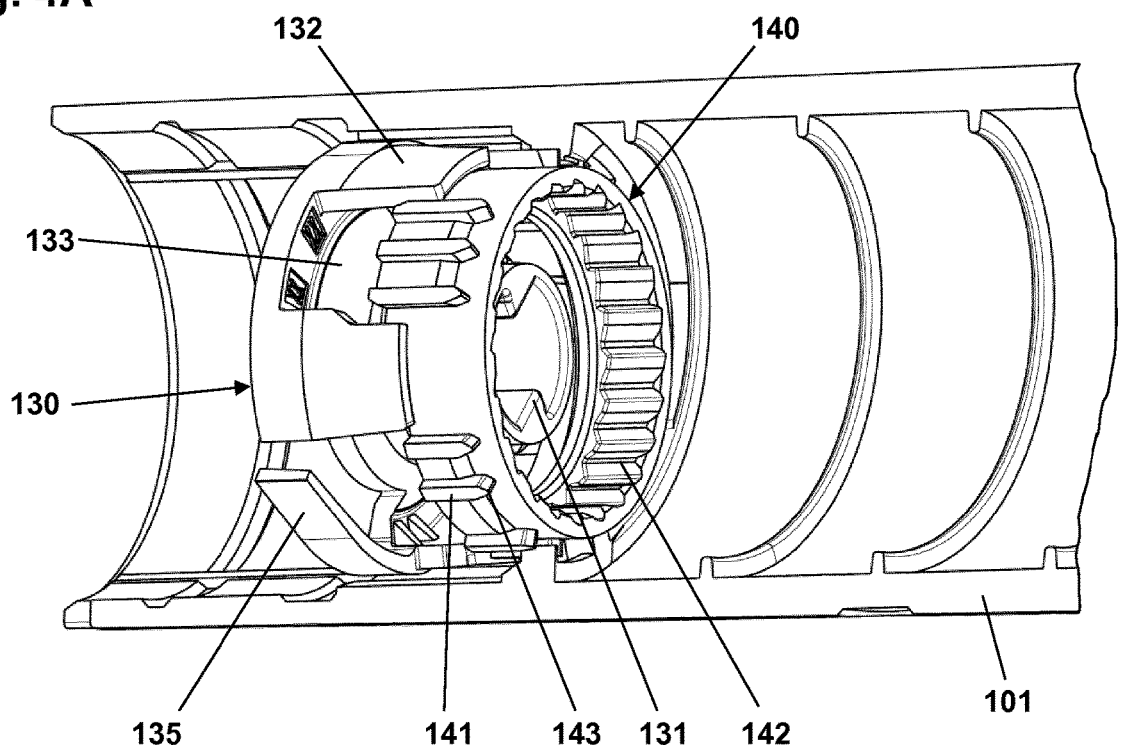
FIGS. 4A-4C show components of the pen device of FIG. 2.
Figure 4B:
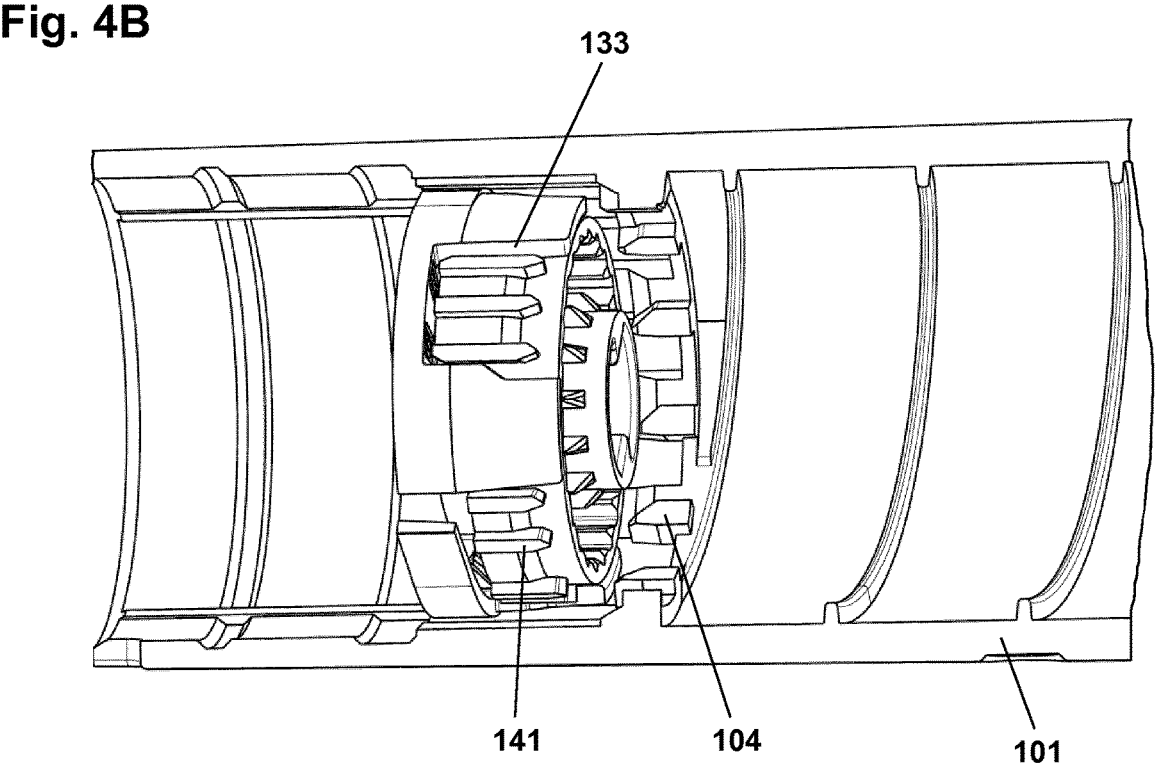
Figure 4C:
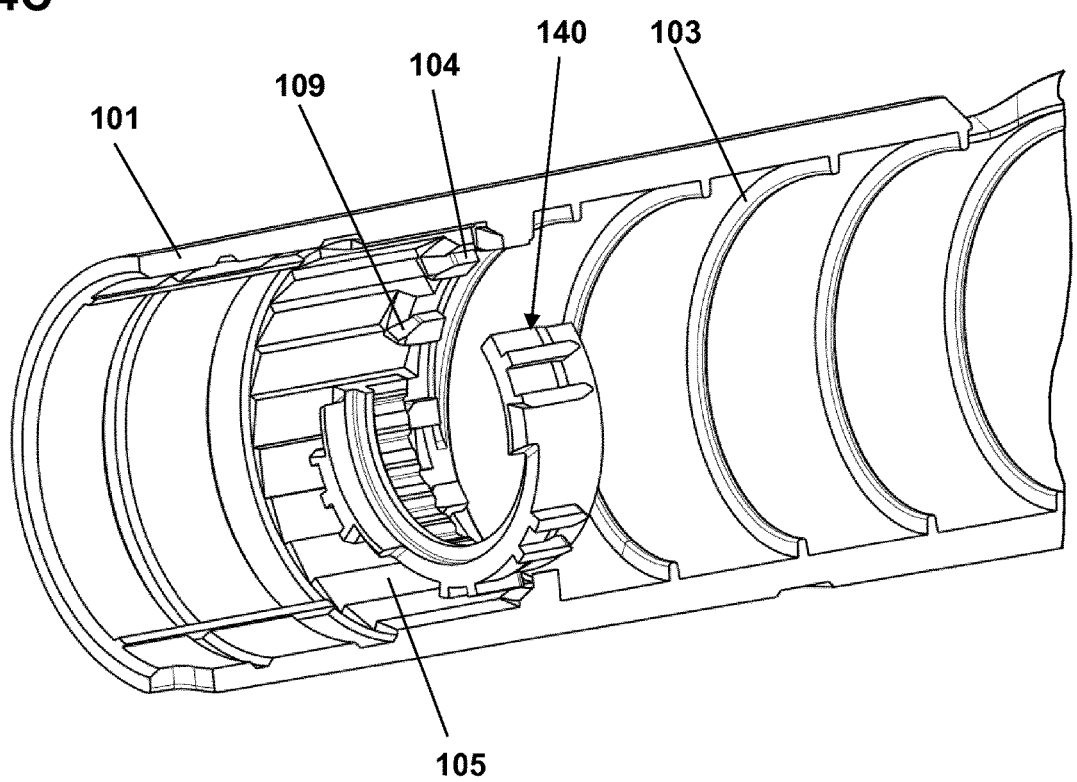

In FIG. 4A the clutch element, the drive element and the housing (in partial) are shown in the dose setting state, and in FIG. 4B the same components are shown in the expelling state. As appears, the piston rod on which the drive element is arranged and the ratchet tube on which the clutch element is mounted are not shown. To better show the structures provided on the inner surface of the housing FIG. 4C shows a partial clutch element 140 arranged in the housing 101.

The inner surface of the housing 101 comprises a circumferential ring-formed array of axially oriented spline elements 104 protruding into the interior, each having a pointed distal end 109, as well as a circumferential ring-formed array of one-way ratchet teeth 105. The inner surface further comprises a male helical thread 103 adapted to engage the female helical thread 173 on the scale drum 170. A distal circumferential groove is formed to engage and mount the nut element 125. The clutch element 140 comprises an inner circumferential ring-formed array of ratchet teeth 142 adapted to engage the ratchet arm 152 on the ratchet tube 150, and an outer circumferential ring-formed array of axially oriented spline elements 141 adapted to engage the spline elements 104 of the housing as well as the coupling slots in the drive element (see below), each spline having a pointed proximal end 143. The drive element 130 comprises a pair of opposed coupling portions each comprising two proximally extending skirt portions 132 between which an axially extending coupling slot 133 is formed, the slot being adapted to engage a portion of the clutch element spline elements. In this way the engaging surfaces serve to transmit a rotational force and thereby torque from the clutch element to the drive element in the expelling state. The drive element further comprises a pair of opposed circumferentially extending flexible ratchet arms adapted to engage the ring-formed array of one-way ratchet teeth 105. During dose delivery, the drive element rotates anti-clockwise and the ratchet arms 135 also provide the user with small clicks due to the engagement with the ratchet teeth 105, e.g. one click per unit of insulin expelled. In the shown embodiment 24 ratchet teeth are provided corresponding to 15 degrees rotation per unit of insulin. The central bore of the drive element comprises two opposed protrusions 131 adapted to engage with the axially oriented grooves on the piston rod.

In the dose setting state shown in FIG. 4A the spline elements 141 of the clutch element are in engagement with the spline elements 104 of the housing thereby rotationally locking the clutch element relative to the housing. As can be seen from FIG. 4A a group of clutch spline elements are received in the corresponding coupling slot with a slight rotational play. In the expelling state shown in FIG. 4B the spline elements 141 of the clutch element are moved distally out of engagement with the spline elements 104 of the housing thereby allowing rotation of the clutch element relative to the housing. As can be seen from FIG. 4B the group of clutch spline elements are now received in the corresponding coupling slot without rotational play.

When a dose has just been expelled movement of the clutch element has stopped but it is still in its distal position. Subsequently, when the user releases pressure on the release button the clutch element returns to its proximal position, however, due to the definite number of splines the clutch element will often rotate a small amount when doing so. Correspondingly, the expelling mechanism is not in a stable condition until the clutch element has returned to the initial proximal position.

Having described the working principles of a mechanical drug delivery device, exemplary embodiments of the present invention will be described.

As appears from the above description of a drug delivery device comprising components which rotate in a first direction during dose setting and in the opposite direction during dose expelling, the rotational positions between the beginning and the end of an out-dosing event would be indicative of the amount of drug expelled and, most likely, injected.

Correspondingly, in accordance with a first aspect of the present invention, an embodiment of a drug delivery device will be described which in a simple and cost-effective way is adapted to detect the size of an expelled dose of drug. More specifically, a drug delivery device is provided with a stationary sensor assembly and a moveable indicator element in the form of a slightly modified reset tube essentially corresponding to the above-described reset tube 160, the modified reset tube comprising an outer surface allowing movement to be detected by sensor circuitry.

Figure 5:
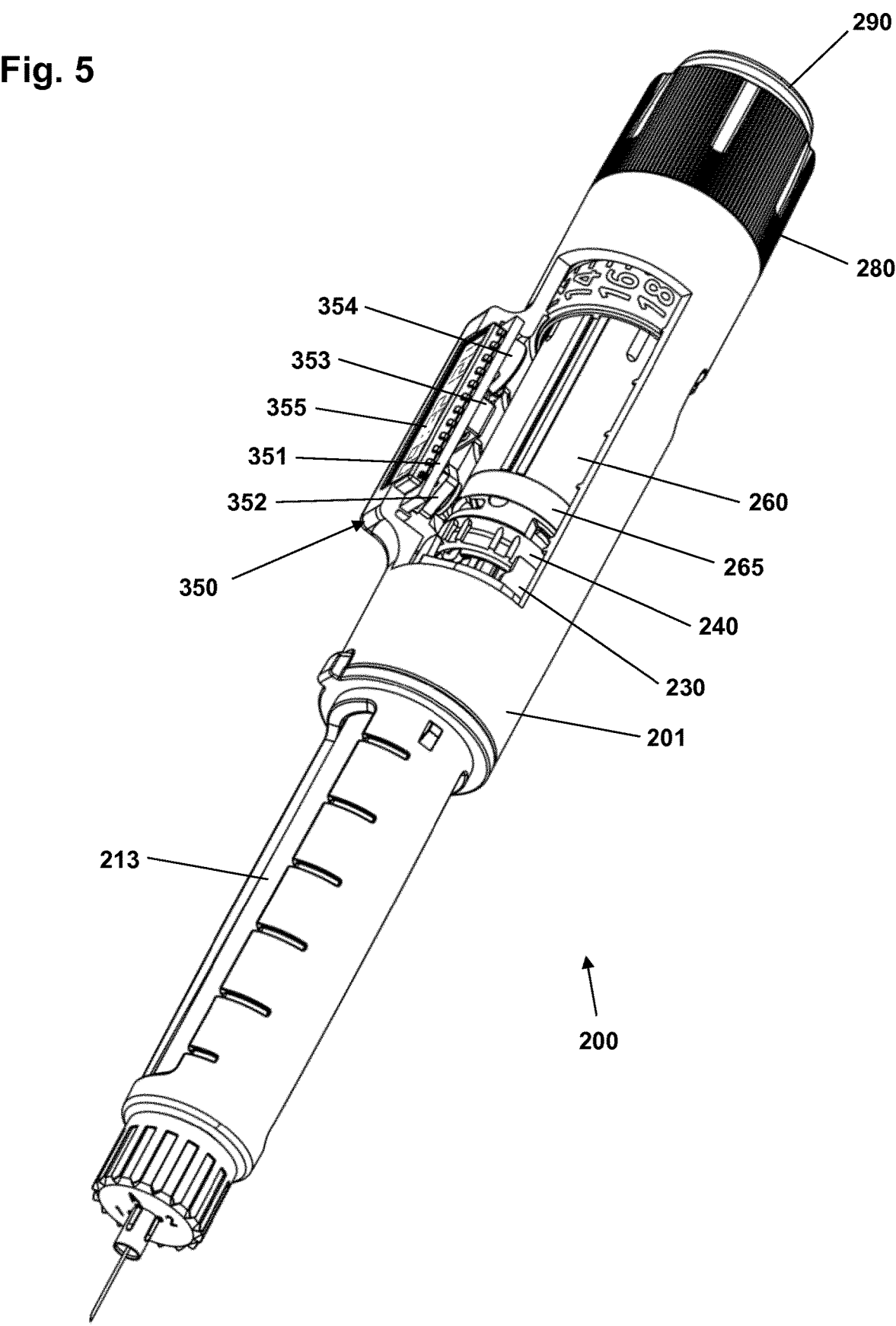
FIG. 5 shows a drug delivery device comprising a sensor system.

Turning to FIG. 5 a drug delivery device 200 of the same general design as the drug delivery device 100 described with reference to FIGS. 1-4C is shown, the drug delivery device 200 additionally comprising electronic sensor circuitry 350 mounted in a piggyback extension of a modified housing 201, wherein the electronic sensor circuitry is adapted to detect movement of the reset tube 260. As described above, the reset tube is arranged to rotate during dose setting, to move axially during dose release, and to rotate during dose expelling corresponding the amount of drug being expelled, the reset tube thereby serving as a dose indicator allowing the size of an expelled dose of drug to be determined.

In the shown embodiment the electronic sensor circuitry comprises a circuit board 351 on which an optical sensor unit 352 capable of detecting motion and accurately measure speed of motion of a surface moving relative to the sensor unit in one or two directions. Based on these measurements, the sensor electronics is able to integrate the measured velocities over the time measured and calculate the distance of relative motion very accurately. The sensor circuitry further comprises a processor 353, an energy source, e.g. a button cell 354, and a display 355 adapted to display dose related information, e.g. time and size for the last expelled dose. Instead of a display or in addition to the display the sensor electronics may be adapted to communicate (wirelessly) with external devices, e.g. a smartphone using Bluetooth® Low Energy (BLE).

The sensor may be of the same type as commonly used in a computer mouse. They offer very accurate tracking on practically any (smooth) surface. Where earlier optical mouse sensors were based on imaging chips taking snapshots of the surface and measuring how the image of the surface had moved between two images, a new generation of optical sensors are based on small lasers and the measurement of interference due to the Doppler effect. A description of the working principal and the fundamentals for such sensors can be found in an article in Hindawi Journal of Sensors: "Experimental Characterization of the Twin-Eye Laser Mouse Sensor" by Javier Moreno, Eduard Clotet, Dani Martinez, Marcel Tresanchez, Tomas Palleja and Jordi Palacfn, to which reference is made. Examples of commercially available sensors of this type are PLN3032 and PLN2020 manufactured and marketed by Phillips. These components are in fact complete sub-systems comprising embedded software for e.g. power management and port communication with external components. The shown sensor unit is a relatively large standard unit measuring 6×6×4 mm and intended to be used for standard applications in e.g. computer mice and printers for which small size is not required, however, a purpose made unit could be made significantly smaller.

In the shown embodiment the optical sensor unit 352 is arranged corresponding to the distal end of the reset tube 260, the modified reset tube comprising at the distal end a smooth circumferential ring-formed surface portion 265 without any additional structures such as grooves or openings, this allowing un-interrupted detection of movement of the ring-formed portion of the reset tube.

The sensor system powers on in short regular intervals to check if there is any current movement of the reset tube 260. The system measures movement using a relatively low measuring resolution to save power, since accuracy of measurement is not important to determine if the reset tube moves or not. When the pen device is not in use there is no motion of the reset tube and the system goes back to power save or idle mode immediately after having established no current motion.

When the user dials a dose by rotating the dose setting member 280, the reset tube 260 rotates inside the clutch element 240. A short power-up every second or two in low-power state would allow rotational movement of the reset tube to be detected in case the sensor arrangement is set up correspondingly, i.e. the reset tube when rotated serves as an "alert indicator" for waking up the system. For example, if rotational movement is detected the sensor system may enter an "alert mode" in which the system will power-up to low-power mode with a higher frequency, this allowing a potential relatively fast and relatively short axial movement of the reset tube to be detected with a high degree of certainty, this allowing the sensor system to enter the high-power measuring state ready to detect an imminent release of the reset tube and thus a relatively fast rotation of the reset tube during expelling of a set dose amount. Axial movement of the reset tube could be monitored by e.g. using a twin-eye sensor able to measure motion corresponding to two orientations.

In case only the initial rotational movement of the reset tube during dose setting, and not the axial movement of the reset tube during dose release, is used as an activation indicator, it may be advantageous that two different rotational members are used as otherwise the system would have to analyse whether a given rotation is due to dose setting or dose expelling. For the shown embodiment, the clutch member could then be used as the indicator.

As appears, using detection of an initial movement of an alert indicator, e.g. a dose setting member, to enter an alert mode requires the drug delivery device to be used in a specific way, i.e. the user uses the dose setting member to set a dose shortly after which the release member is actuated to expel the set dose. However, in case the set dose is not expelled immediately after having been set, the alert mode may time out, and e.g. axial movement of the activation sensor may not be detected.

Correspondingly, at the cost of slightly higher power consumption, a system set-up allowing movement of an activation indicator to be detected with the sensor circuitry in idle mode would provide a system adapted to capture the size of an expelled dose amount in a safe and reliable way without having to rely on the user operating the drug delivery device in a specific required way.

In the following an exemplary use scenario will be described.

When the user picks up the pen device 200 to set and subsequently expel a dose of drug, the sensor system 350 is in an "idle mode" in which it shortly enters a low-power state at predetermined intervals, e.g. every second or two, to detect potential movement of the reset tube. If no movement is detected the sensor system will revert to sleep state.

Figure 6A:
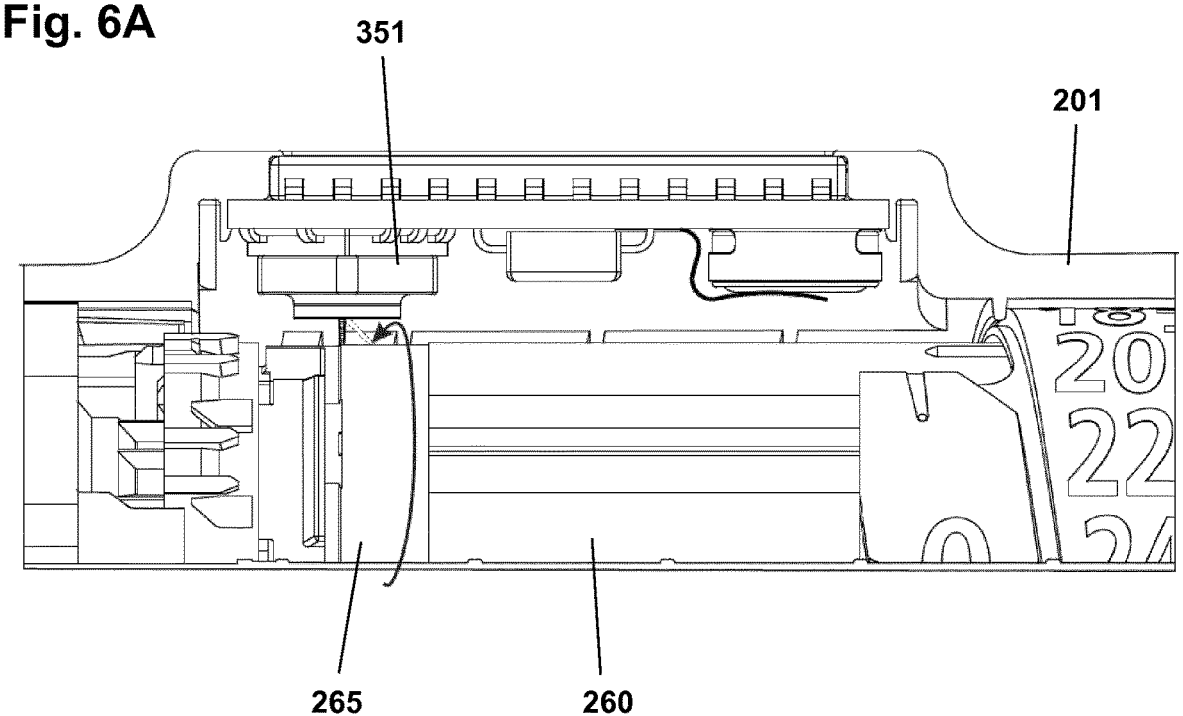
FIGS. 6A-6C show in partial cut-away views the sensor system of FIG. 5 in different operational states.

When the user starts dialling a dose, the system may be designed to detect rotational movement of the reset tube 260 during the short low-power low-performance wake-ups performed every second or two, this preparing the system to expect a dose release in the near-future, see FIG. 6A. The system may then switch to high-power high-performance mode or just reduce the time between wake-ups corresponding to an "alert mode". Alternatively, initial rotational movement during dose setting may not be detected.

Figure 6B:
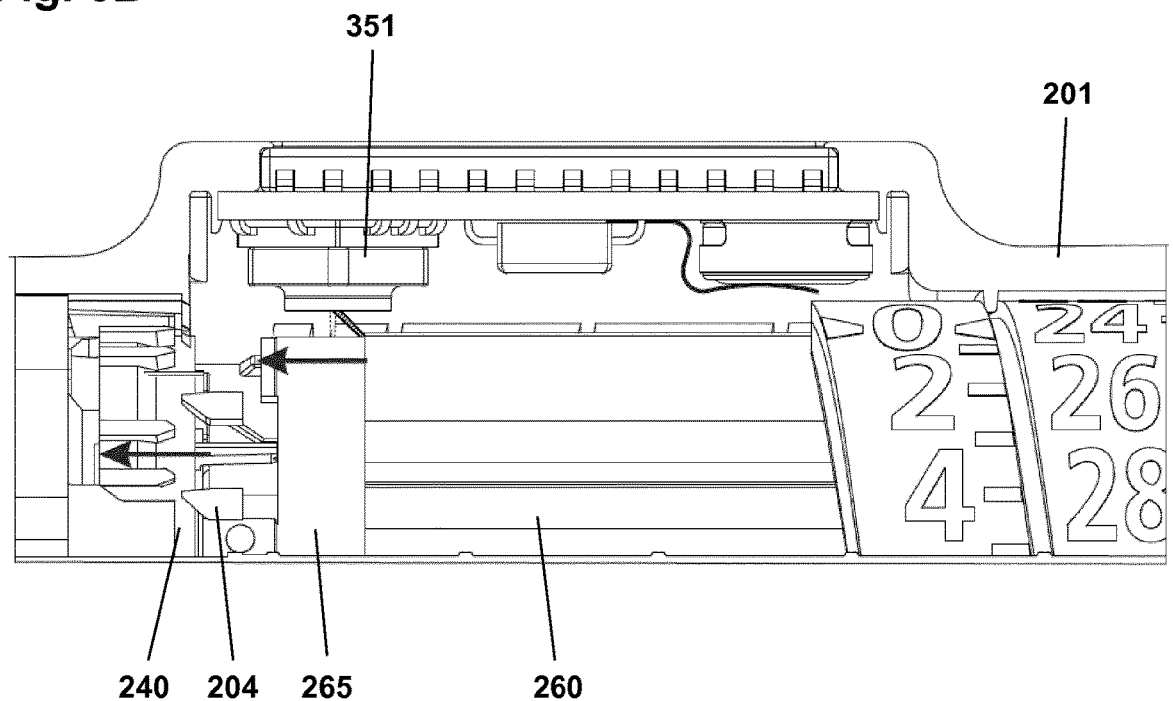

When the user has dialed a dose and inserted the needle subcutaneously, the user pushes the dose release button 290, this resulting in the reset tube 260 being moved forward to move the clutch element 240 out of engagement with the housing splines 204, see FIG. 6B. This axial movement is then detected by the sensor system thereby switching the system into high-power high-performance measuring mode.

Figure 6C:
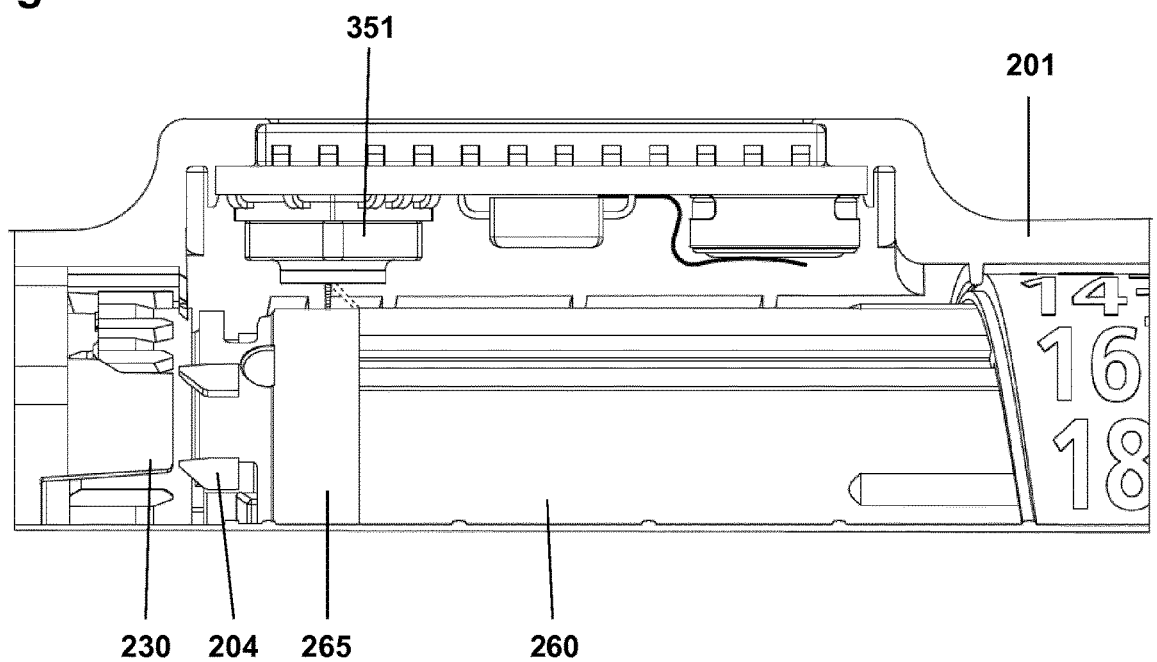

When the clutch element 240 has disengaged the housing, the reset tube starts driving the clutch element, now engaged with the ring-formed piston rod drive element 230. The rotational movement of the reset tube is thus transmitted to the piston rod and due to the piston rod threading and its engagement with the nut, the reset tube thereby driving the piston rod distally and drug is expelled. The sensor system in high-power high-performance measuring state now measures very accurately the rotational speed and calculates the "surface distance" of the reset tube portion 265 passing the sensor in rotational direction, see FIG. 6C.

At end-of-dose movement of the reset tube stops 260 which can be used to end measurement and calculate the amount of rotational movement. The expelled dose can then be calculated by dividing the total travelled distance of the reset tube surface 265 by its circumference, multiply it by 360 degrees pr. full rotation, and divide the result by the number of degrees per unit/amount of drug. The result may then be rounded to the nearest integer number of units, since the device is only intended to administer an integer number of units. The actual calculation of dose amounts may be done by the sensor electronics or by e.g. an external device receiving the "raw" measurement data.

Alternatively the sensor system can detect axial movement of the reset tube when the dose release button is released and the reset tube pulls the clutch element back into engagement with the device housing, and then calculate the travelled distance/expelled dose from the total rotationally travelled distance of the reset tube surface.

When dose button release is completed, the display can be changed to display the size and time of the just administered dose.

In the shown embodiment the sensor system comprises a twin-eye laser sensor with a first beam dedicated to detection and measurement of rotational movement corresponding to a first orientation and a second beam dedicated to detection of axial movement corresponding to a second orientation.

Figure 7:
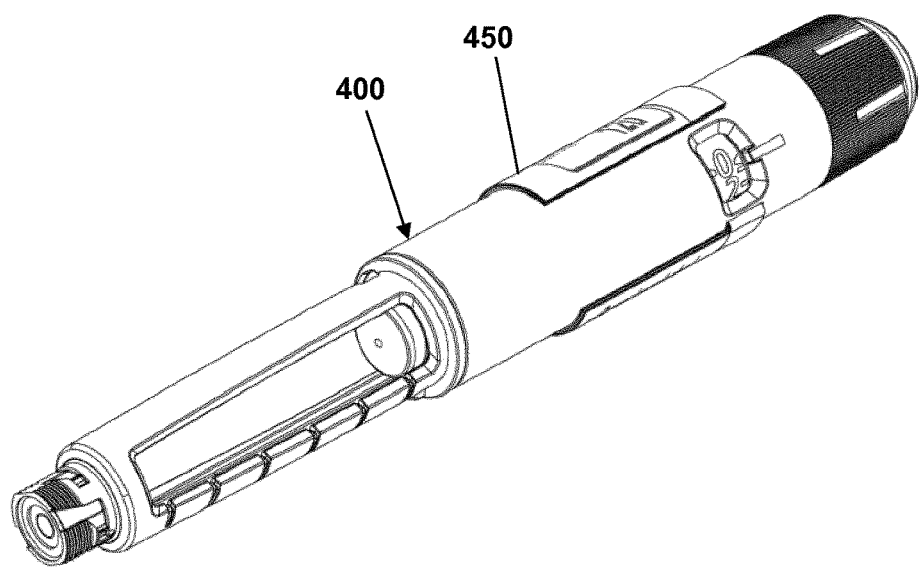
FIG. 7 shows a drug delivery device comprising a sensor system in the form of an electronic label.

As described above, the embodiment shown in FIG. 5 is build using rather bulky standard components, however, with a custom design of the sensors as well as the additional structures, e.g. power source, processor, display and antenna, it may be possible to substantially reduce both size and cost of the measuring system, e.g. in the form of an "electronic label" 450 attached to a pen device 400 as shown in FIG. 7.

The display may be of the printed ink-type which mainly uses energy when changing state. An antenna may also be formed on the flexible sheet by printing, the processor being adapted to transmit data to an external receiver via the antenna. The design and manufacture of an "electronic label" incorporating e.g. printed electronics is described in greater detail in WO 2015/071354 which is hereby incorporated by reference.

Figure 8:
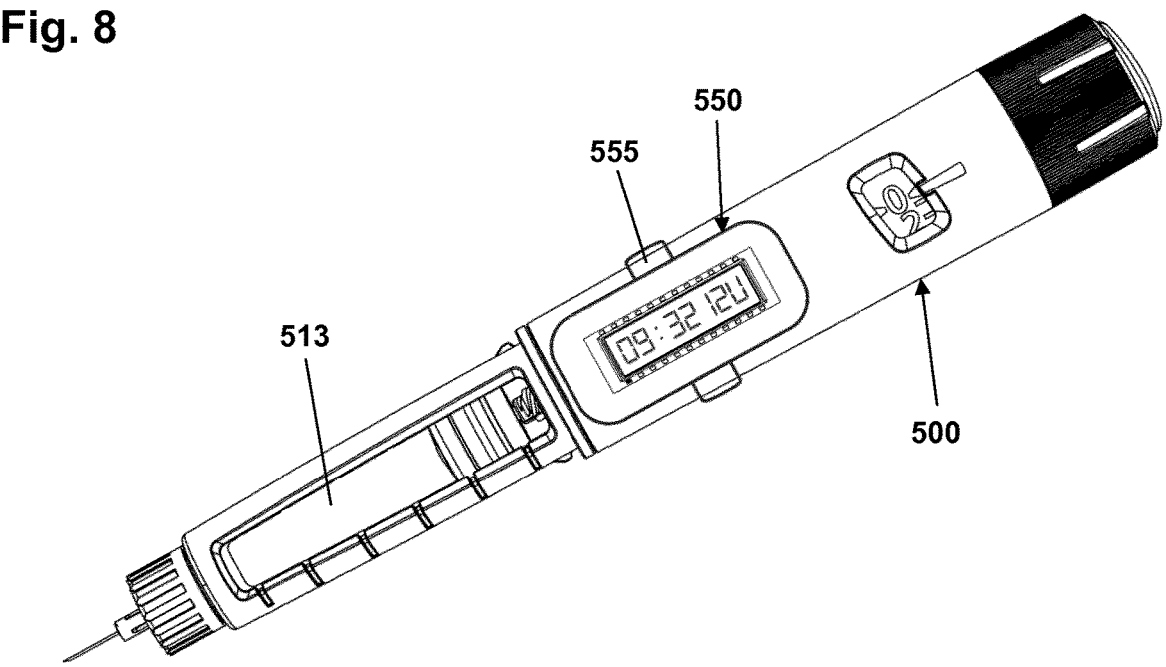
FIG. 8 shows a first embodiment of a drug delivery assembly comprising an add-on dose capture unit.

FIG. 8 shows an alternative embodiment in which the measuring device is provided as a separate add-on unit 550 adapted to be releasably mounted on a corresponding pen device 500 which may be either prefilled and thus disposable or durable and thus adapted to receive a drug cartridge 513. Corresponding to the above-described integrated embodiment the pen device comprises a modified reset tube allowing for optical detection of reset tube movement. Additionally, the housing is provided with an opening (not seen) allowing the distal portion of the reset tube to be viewed by the optical unit. The opening may initially be covered by the otherwise present product label and be punctured when the add-on device is mounted. Indeed, the pen device and the add-on device are provided with corresponding coupling means 455 allowing the add-on device to be safely and securely mounted in a predefined position. Otherwise the add-on device may be identical to the above-described integrated sensor device.

Figure 9:
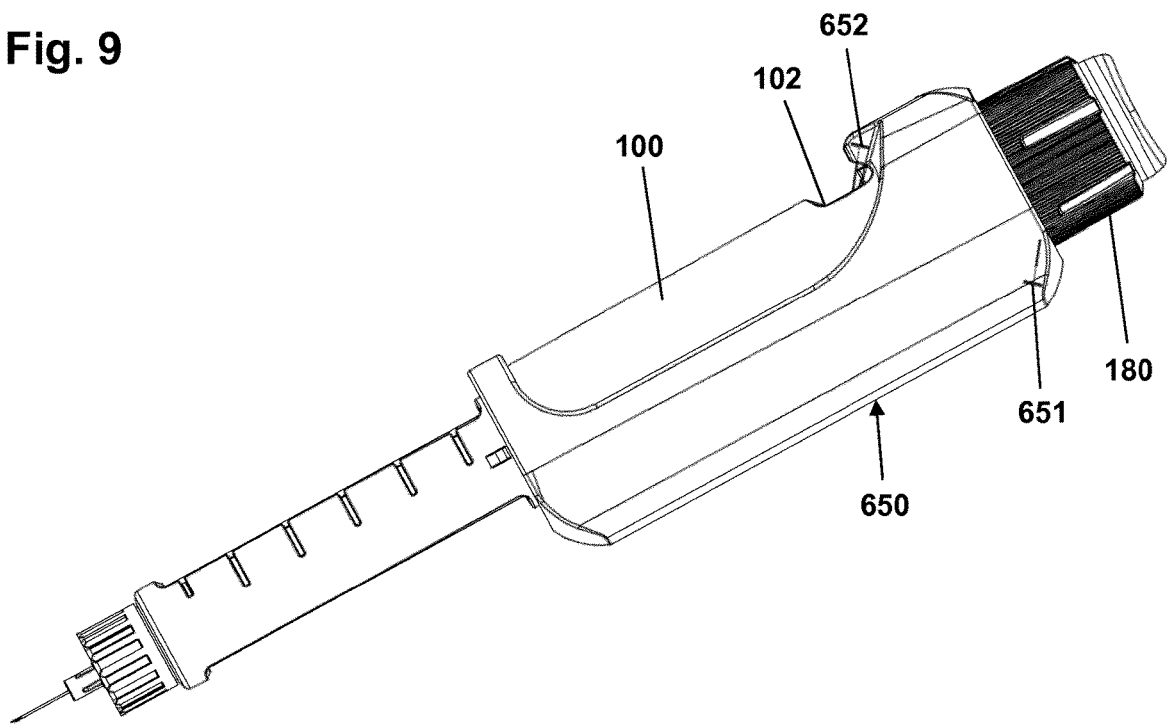
FIG. 9 shows a second embodiment of a drug delivery assembly comprising an add-on dose capture unit.

FIG. 9 shows a further embodiment in which the measuring device is provided as a separate add-on unit 650 adapted to be releasably mounted on an un-modified pen device 100 which may be either prefilled or durable. In contrast to the above-described embodiment utilizing a single sensor unit, the add-on embodiment of FIG. 9 comprises two separate sensor units, the first unit 651 being a wake-up dedicated sensor arranged to detect movement of the dose setting member 180, the second sensor unit 652 being arranged and adapted to measure rotation of the scale drum as it passes the window opening 102 during expelling of a dose of drug.

For example, when movement of the dose setting member is detected, the first sensor may be switched to a higher-frequency alert mode adapted to detect when rotation of the dose setting member stops, this indicating that a dose has been set resulting in the second sensor unit being switched to high-power high-performance measuring mode. As the scale drum typically will rotate much faster during expelling of drug a "true" expelling event can be detected. Otherwise, if the scale drum rotates only slowly (or in the opposite direction) this would indicate that the user has not yet finished setting a dose and the system will revert to alert mode.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A drug delivery assembly, comprising:
   a housing,
   a drug reservoir or structure for receiving a drug reservoir,
   drug expelling structure comprising dose setting structure allowing a user to set a dose amount of drug to be expelled, and release structure which when actuated causes:
      movement of an activation indicator, and
      the drug expelling structure to expel a set dose,
   a dose indicator adapted to move during expelling of a dose amount of drug, the amount of movement being indicative of the size of the expelled dose amount, and
   electronic sensor circuitry adapted to detect the amount of movement of the dose indicator during expelling of a dose amount,
   wherein:
      the electronic sensor circuitry comprises a light-based non-contact tracking structure adapted to determine a motion property of a surface moved relative to the tracking structure,
      the electronic sensor circuitry can be operated between:
         a sleep state,
         a low power detection state allowing a first motion property to be determined, and
         a high power measuring state allowing a second motion property to be determined,
      the electronic sensor circuitry with pre-determined intervals is adapted to change the operative state from the sleep state to the detection state and back to the sleep state,
      when in the detection state, the electronic sensor circuitry is adapted to detect whether motion of the activation indicator relative to the tracking structure takes place, and
      if motion of the activation indicator is detected, the electronic sensor circuitry is adapted to change the operative state from the detection state to the measuring state in which the amount of motion of the dose indicator relative to the tracking structure can be determined.

2. The assembly as in claim 1, wherein the dose indicator rotates during dose expelling, the electronic sensor circuitry being adapted to determine the amount of rotation.

3. The assembly as in claim 1, wherein the dose setting structure comprises a dose setting member adapted to be rotated by a user to set a dose, the release structure further comprising:
   a release member actuatable between a proximal position and a distal position, the proximal position allowing a dose amount to be set by rotation of the dose setting member, the distal position allowing the drug expelling structure to expel a set dose.

4. The assembly as in claim 3, wherein rotation of the dose setting member causes motion of the activation indicator.

5. The assembly as in claim 3, wherein actuation of the release member causes motion of the activation indicator.

6. The assembly as in claim 1, wherein the dose indicator rotates during dose expelling relative to a reference axis and the activation indicator moves axially relative to the reference axis.

7. The assembly as in claim 6, wherein the activation indicator and the dose indicator are coupled to each other forming a combined indicator.

8. The assembly as in claim 1, wherein the drug expelling structure further comprises an alert indicator adapted to move during dose setting, and the electronic sensor circuitry can be operated between an idle mode and an alert mode, wherein:
   when in the idle mode, the electronic sensor circuitry is adapted to change, with pre-determined intervals, the operative state from the sleep state to the detection state and back to the sleep state,
   when in the idle mode and in the detection state, the electronic sensor circuitry is adapted to detect motion of the alert indicator relative to the tracking structure, and if motion of the alert indicator relative to the tracking structure is detected, then change the idle mode to the alert mode in which the electronic sensor circuitry with shortened intervals changes the operative state from the sleep state to the detection state and back to the sleep state, and
   when in the alert mode and in the detection state, the electronic sensor circuitry is adapted to detect motion of the activation indicator relative to the tracking structure, and if motion of the activation indicator relative to the tracking structure is detected, then change the operative state from the detection state to the measuring state in which the amount of motion of the dose indicator relative to the tracking structure can be determined.

9. The assembly as in claim 8, wherein the alert indicator rotates during dose setting.

10. The assembly as in claim 9, wherein the dose indicator rotates during dose expelling relative to a reference axis and the activation indicator moves axially relative to the reference axis, and
    wherein at least two of the activation indicator, the dose indicator and the alert indicator are coupled to each other forming a combined indicator.

11. The assembly as in claim 1, wherein the electronic sensor circuitry when in the low power detection state is operated to detect motion with a low resolution, and when in the high power measuring is operated to detect motion with a high resolution.

12. The assembly as in claim 1, wherein the drug expelling structure and the electronic sensor circuitry both form part of an integrated drug delivery device.

13. The assembly as in claim 1, comprising a drug delivery device and an add-on device adapted to be releasably mounted thereon, the drug delivery device comprising the drug expelling structure and the activation indicator and the dose indicator, the add-on device comprising the electronic sensor circuitry.

14. The assembly as in claim 1, wherein the tracking structure is laser based and the activation indicator and the dose indicator comprise light-scattering surfaces towards which the laser light is directed.

15. The assembly as in claim 1, wherein the drug expelling structure comprises:
    a piston rod adapted to engage and axially displace a piston in a loaded cartridge in a distal direction to thereby expel a dose of drug from the cartridge,
    a drive member,
    a drive spring coupled to the drive member,
    the dose setting structure allowing a user to simultaneously set a dose amount to be expelled and strain the drive spring correspondingly by rotation of the drive member, and
    the release structure adapted to release the strained drive spring to rotate the drive member to expel the set dose amount.

\* \* \* \* \*

UNITED STATES PATENT AND TRADEMARK OFFICE
CERTIFICATE OF CORRECTION

| | | |
|---|---|---|
| PATENT NO. | : 12,239,827 B2 | Page 1 of 1 |
| APPLICATION NO. | : 17/056319 | |
| DATED | : March 4, 2025 | |
| INVENTOR(S) | : Larsen | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1141 days.

Signed and Sealed this
Seventh Day of October, 2025

John A. Squires
*Director of the United States Patent and Trademark Office*